United States Patent
Coffindaffer et al.

(10) Patent No.: US 9,585,823 B2
(45) Date of Patent: Mar. 7, 2017

(54) PERSONAL CARE COMPOSITIONS COMPRISING A MULTI-ACTIVE SYSTEM FOR DOWN REGULATING CYTOKINES IRRITATION

(75) Inventors: Timothy Woodrow Coffindaffer, Maineville, OH (US); Benjamin Parker Heath, Cincinnati, OH (US); Helen Rochelle Kemp, Glendale, OH (US); Robert John Willicut, Liberty Township, OH (US)

(73) Assignee: The Gillette Company, Boston, MA (US)

( * ) Notice: Subject to any disclaimer, the term of this patent is extended or adjusted under 35 U.S.C. 154(b) by 1060 days.

(21) Appl. No.: 12/984,958

(22) Filed: Jan. 5, 2011

(65) Prior Publication Data

US 2011/0162668 A1   Jul. 7, 2011

Related U.S. Application Data

(60) Provisional application No. 61/293,025, filed on Jan. 7, 2010.

(51) Int. Cl.

| | |
|---|---|
| *A61K 8/39* | (2006.01) |
| *A61K 8/34* | (2006.01) |
| *A61K 8/891* | (2006.01) |
| *A61K 8/92* | (2006.01) |
| *A61K 8/97* | (2006.01) |
| *A61Q 9/02* | (2006.01) |
| *A61Q 19/00* | (2006.01) |

(52) U.S. Cl.
CPC .................. *A61K 8/39* (2013.01); *A61K 8/34* (2013.01); *A61K 8/891* (2013.01); *A61K 8/922* (2013.01); *A61K 8/97* (2013.01); *A61Q 9/02* (2013.01); *A61Q 19/00* (2013.01); *A61K 2800/75* (2013.01)

(58) Field of Classification Search
USPC .......................................... 132/200; 424/756
See application file for complete search history.

(56) References Cited

U.S. PATENT DOCUMENTS

| | | | |
|---|---|---|---|
| 2004/0265264 A1* | 12/2004 | Sugar et al. | 424/70.22 |
| 2008/0069784 A1* | 3/2008 | Millikin et al. | 424/59 |
| 2008/0206371 A1* | 8/2008 | Fontaine et al. | 424/744 |
| 2008/0317681 A1* | 12/2008 | Gebreselassie et al. | 424/48 |
| 2009/0220625 A1 | 9/2009 | Herrmann et al. | |

OTHER PUBLICATIONS

PCT International Search Report dated Aug. 17, 2012.

* cited by examiner

*Primary Examiner* — Michael G. Hartley
*Assistant Examiner* — Robert Cabral
(74) *Attorney, Agent, or Firm* — Ronald T. Sia; Kevin C. Johnson; Steven W. Miller

(57) ABSTRACT

A personal care composition comprising a multi-active system for down regulating cytokines comprising: bis-abolol and ginger extract, and a surfactant derived from a triglyceride such as olive oil, and methods of use.

14 Claims, No Drawings

PERSONAL CARE COMPOSITIONS COMPRISING A MULTI-ACTIVE SYSTEM FOR DOWN REGULATING CYTOKINES IRRITATION

CROSS REFERENCE TO RELATED APPLICATIONS

This application claims the benefit of U.S. Provisional Application No. 61/293,025 filed on Jan. 7, 2010.

BACKGROUND OF THE INVENTION

Currently there are a number of personal care compositions which can be used either during the shaving process or before/after shaving. These compositions include pre-shaving moisturizers and balms as well as skin and facial cleansers; shaving oils, foams and gels; and post-shave moisturizers and lotions. Many of these compositions focus on moisturizing the skin and hair prior to shaving to decrease the cutting force required to shave the hairs and lubricating the skin to reduce irritation which may occur from contact with the razor blade. Numerous shave preparation and cosmetic compositions have been described. See e.g. U.S. Patent Publ. Nos. 2008/0069784 and 2005/0019356A1, see also U.S. Patent Publ. 2009/0197939A1, 20090117061, 20090220625, and 20080253973; and WO 10/073278; 09/093104; and Ser. No. 09/094,238. Despite the many attempts to create personal care compositions which can be used for shave preparation, there remains a need for compositions which reduce skin irritation.

SUMMARY OF THE INVENTION

One aspect of the present invention provides for a personal care composition which is suitable for various uses including but not limited to facial or body cleansers or scrubs, pre-shave preparations, shaving gels or foams, moisturizers and lotions, and so forth, said personal care composition comprising: from about 0.001% to about 10% of a multi-active system for down regulating cytokines, said multi active system comprising: bis-abolol and ginger extract, and a surfactant derived from a triglyceride, such as olive oil; and a carrier which is acceptable for such personal care and cosmetic purposes. One suitable example of a surfactant derived from olive oil is sodium polyethylene glycol 7 olive oil carboxylate.

Another aspect of the present invention provides for a method of reducing or controlling skin irritation by applying a personal care composition of the present invention onto skin to form a treated surface. Where the invention is used in a shaving context, the treated surface can then be shaved with a razor.

DETAILED DESCRIPTION OF THE INVENTION

The personal care composition of the present invention comprises a multi-active system for down regulating cytokines. Without intending to be bound by theory, it is believed that by including multiple actives the ability of each active to reduce skin inflammation is increased such that the combined use of the multiple actives exceeds the benefit obtained by using each active separately. The multi-active system for down regulating cytokines comprises at least two actives: bis-abolol and ginger extract, and a surfactant derived from a triglyceride, one suitable triglyceride is olive oil. The personal care composition of the present invention comprises from about 0.001% to about 10%, or from about 0.005% to about 5%, or from about 0.01% to about 3%, or from about 0.1% to about 2%, or from about 0.2% to about 1.0%, or from about 0.25% to about 0.5% by weight of the multi-active system, by weight of the total composition.

1. Multi-Active System for Down Regulating Cytokines a. Bis-Abolol and Ginger Extract

The multi-active system of the present invention may include a safe and effective amount of bis-abolol and ginger extract. When present, the composition contains bis-abolol and ginger extract in an amount of from about from about 0.001% to about 10%, or from about 0.005% to about 5%, or from about 0.01% to about 3%, or from about 0.1% to about 2%, or from about 0.2% to about 1.0%, or from about 0.25% to about 0.5%, by weight of the total composition.

The primary components of ginger extract (*Zingiber officinale* Rosc.) are gingerols and shogaols. The structures of Bis-abolol, gingerol, and shogaol are shown below:

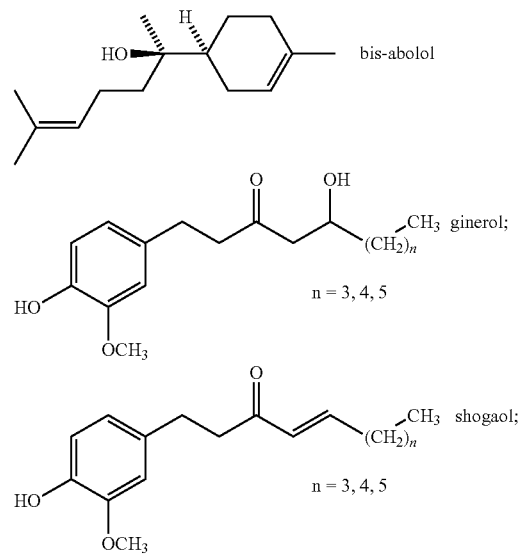

Bis-abolol and ginger extract acts as an anti-inflammatory, inhibiting both IL-1α and PGE-2. An example of a bis-abolol and ginger extract useful herein is Symrelief, which can be purchased from Symrise, Marlow, Buckinghamshire, UK.

b. Surfactant Derived from a Triglyceride

The multi-active of the present invention also comprises a surfactant derived from a triglyceride. The triglyceride of the present invention comprises a multiple fatty acids: Oleic fatty acid, linoleic fatty acid, linolenic acid and combinations thereof. Preferably the majority of the fatty acids are the oleic and linoleic fatty acids. The anionic surfactant is formed by isolating the alkyl chains from the triglyceride into fatty acids, methyl ethers, or fatty alcohols by hydrolysis. The isolated alkyl chains are then ethoxylated. The ethoxylated alkyl chain is then carboxylated. In one embodiment, the anionic surfactant comprises the product of ethoxylating then carboxylating oleic acid. In one embodiment the anionic surfactant is Sodium Polyethylene glycol 7 Olive Oil Carboxylate. In one embodiment, the triglyceride is predominantly unsaturated. "Predominantly unsaturated" as defined herein means that at least 50% by weight of the triglyceride used to make the surfactant is not saturated. Those of skill in the art will also understand that predominantly unsaturated triglycerides include monounsaturated fats and polyunsaturated fats, and tend to be liquid at room temperature. One suitable surfactant derived from a triglyceride is Olivem® 450 and 460 by B&T Company of Milan, Italy.

Suitable predominantly unsaturated triglycerides include plant derived oils such as castor oil, corn oil, oiticica oil, olive oil, linseed oil, cotton seed oil, palm oil, peanut oil, grape seed oil (canola), rice bran oil, safflower oil, sesame oil, sorghum oil, tall oil, tongue oil, soy bean oil, sunflower oil, almond oil, other similarly related vegetable oils and mixtures thereof. Notably, these triglycerides are considered to be saponifiable, thereby resulting in the anionic surfactant. In one preferably embodiment, the triglyceride is olive oil.

In one embodiment, the level of surfactant derived from a triglyceride is amount of from about 0.005% to about 5%, or from about 0.01% to about 3%, or from about 0.1% to about 2%, or from about 0.2% to about 1.0%, or from about 0.25% to about 0.5% by weight of the total composition. In another embodiment, the level of the bis-abolol and ginger extract to the surfactant derived from olive oil is from about 0.01 to 1 to about 1 to 0.01, or from about 4 to 1 about to 1 to 2, or about 1:1.

c. Optional Skin Care Actives

In one embodiment, the personal care composition further comprises one or more additional skin care actives which are commonly used in cosmetic and personal care compositions on the market today. Each of the one or more optional skin care actives can be provided at from about 0.001% to about 10%, or from about 0.1% to about 1% by weight of the composition. Non-limiting examples of suitable actives include one or more of: Lauryl p-Cresol Ketoxime, 4-(1-Phenylethyl)1,3-benzenediol, Lupin (*Lupinus albus*) oil & wheat (*Triticum vulgare*) germ oil unsaponifiables, Hydrolyzed lupin protein, Extract of L-lysine and L-arginine peptides, Oil soluble vitamin C, *Evodia rutaecarpa* fruit extract, Zinc picolate and zinc PCA, Alpha-linoleic acid, p-thymol, and combinations thereof; at least one additional skin and/or hair care active selected from the group consisting of sugar amines, vitamin $B_3$, retinoids, hydroquinone, peptides, farnesol, phytosterol, dialkanoyl hydroxyproline, hexamidine, salicylic acid, N-acyl amino acid compounds, sunscreen actives, water soluble vitamins, oil soluble vitamins, hesperedin, mustard seed extract, glycyrrhizic acid, glycyrrhetinic acid, carnosine, Butylated Hydroxytoluene (BHT) and Butylated Hydroxyanisole (BHA), menthyl anthranilate, cetyl pyridinium chloride, tetrahydrocurmin, vanillin or its derivatives, ergothioneine, melanostatine, sterol esters, idebenone, dehydroacetic acid, Licohalcone A, creatine, creatinine, feverfew extract, yeast extract (e.g., Pitera®), beta glucans, alpha glucans, diethylhexyl syringylidene malonate, erythritol, p-cymen-7-ol, benzyl phenylacetate, 4-(4-methoxyphenyl)butan-2-one, ethoxyquin, tannic acid, gallic acid, octadecenedioic acid, p-cymen-5-ol, methyl sulfonyl methane, an avenathramide compound, fatty acids (especially polyunsaturated fatty acids), anti-fungal agents, thiol compounds (e.g., N-acetyl cysteine, glutathione, thioglycolate), other vitamins (vitamin B 12), beta-carotene, ubiquinone, amino acids, their salts, their derivatives, their precursors, and/or combinations thereof; and a dermatologically acceptable carrier. These and other potentially suitable actives are described in greater detail in U.S. Patent Publication No. 2008/0069784.

2. Carrier

The personal care compositions of the present invention also comprise a carrier for the multi-active system for down regulating cytokines. The carrier is preferably dermatologically acceptable, meaning that the carrier is suitable for topical application to the keratinous tissue, has good aesthetic properties, is compatible with the actives of the present invention and any other components, and will not cause any safety or toxicity concerns. In one embodiment, the personal care composition comprises from about 50% to about 99.99%, preferably from about 60% to about 99.9%, more preferably from about 70% to about 98%, and even more preferably from about 80% to about 95% of the carrier by weight of the composition.

The carrier can be in a wide variety of forms. For example, emulsion carriers, including, but not limited to, oil-in-water, water-in-oil, water-in-oil-in-water, and oil-in-water-in-silicone emulsions, are useful herein.

Preferred carriers comprise an emulsion such as oil-in-water emulsions and water-in-oil emulsions, e.g., silicone-in-water or water-in-silicone emulsions. As will be understood by the skilled artisan, a given component will distribute primarily into either the water or oil phase, depending on the water solubility/dispensability of the component in the composition. Oil-in-water emulsions are especially preferred.

Emulsions according to the present invention generally contain a solution as described above and a lipid or oil. Additional lipids and oils may be derived from animals, plants, or petroleum, or mixtures thereof, and may be natural or synthetic. Preferred emulsions also contain a humectant, such as glycerin. Emulsions will preferably further contain from about 0.1% to about 10%, more preferably from about 0.2% to about 5%, of an emulsifier, based on the weight of the composition. Emulsifiers may be nonionic, anionic or cationic. The emulsifier can be a polymer, a surfactant or a mixture thereof. Suitable emulsifiers are disclosed in, for example, U.S. Pat. Nos. 3,755,560, 4,421,769, and McCutcheon's Detergents and Emulsifiers, North American Edition, pages 317-324 (1986).

a. Water-in-Oil Emulsion

Water in oil emulsions are characterized as having a continuous hydrophobic, water insoluble oil phase and a water phase dispersed therein. The "oil phase" can contain oil, silicone or mixtures thereof. The distinction of whether the emulsion is characterized as a water-in-oil or water-in-silicone emulsion is a function of whether the oil phase is composed of primarily oil or silicone. A preferred example of a water-in-silicone emulsion is described below.

1. Continuous Silicone Phase

Preferred water-in-silicone emulsions of the present invention comprise from about 1% to about 60%, preferably from about 5% to about 40%, more preferably from about 10% to about 30%, by weight of a continuous silicone phase. The continuous silicone phase exists as an external phase that contains or surrounds the discontinuous aqueous phase described hereinafter.

The continuous silicone phase contains a silicone elastomer and/or polyorganosiloxane oil. The continuous silicone phase of these preferred emulsions comprises between about 50% and about 99.9% by weight of organopolysiloxane oil and less than about 50% by weight of a non-silicone oil. In a preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and still more preferably less than about 2%, by weight of the continuous silicone phase.

2. Polyorganopolysiloxane Oil

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples include polyalkylsiloxanes, cyclic polyalkylsiloxanes, and polyalkylarylsiloxanes.

Suitable polyalkylsiloxanes include polyalkylsiloxanes with viscosities of from about 0.5 to about 1,000,000 centistokes at 25° C. Commercially available polyalkylsiloxanes include polydimethylsiloxanes, which are also known as dimethicones, examples of which include the Vicasil® series sold by General Electric Company and the DC® 200 series sold by Dow Corning Corporation. Cyclic polyalkylsiloxanes suitable for use in the composition include those commercially available such as DC® 244, DC® 344 fluid, and DC® 345 fluid.

Also useful are materials such as trimethylsiloxysilicate, which is a polymeric material corresponding to the general chemical formula $[(CH_2)_3SiO_{1/2}]_x[SiO_2]_y$, wherein x is an integer of from about 1 to about 500 and y is an integer of from about 1 to about 500. A commercially available trimethylsiloxysilicate is sold as a mixture with dimethicone as DC® 593 fluid.

Dimethiconols are also suitable for use in the composition. These compounds can be represented by the chemical formulas $R_3SiO[R_2SiO]_xSiR_2OH$ and $HOR_2SiO[R_2SiO]_xSiR_2OH$ wherein R is an alkyl group (preferably R is methyl or ethyl) and x is an integer of from 0 to about 500, chosen to achieve the desired molecular weight. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition, particularly those having viscosities of from about 15 to about 65 centistokes at 25° C. Preferred for use herein are organopolysiloxanes selected from the group consisting of polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

As stated above, the continuous silicone phase may contain one or more non-silicone oils. Suitable non-silicone oils have a melting point of about 25° C. or less under about 1 ATM of pressure. Examples of non-silicone oils suitable for use in the continuous silicone phase are those known in the chemical arts in topical personal care products which can be in the form of emulsions, e.g., mineral oil, vegetable oils, synthetic oils, semisynthetic oils, fatty acid esters, etc.

3. Silicone Elastomer

The compositions of the present invention also include from about 0.1% to about 30%, by weight of the composition, of a silicone elastomer component. Preferably, the composition includes from about 1% to about 30%, more preferably from about 2% to about 20%, by weight of the composition, of the silicone elastomer component.

Suitable for use are silicone elastomers, which can be emulsifying or non-emulsifying crosslinked siloxane elastomers or mixtures thereof. No specific restriction exists as to the type of curable organopolysiloxane composition that can serve as starting material for the crosslinked organopolysiloxane elastomer. Examples are addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl-terminated diorganopolysiloxane and SiH-containing diorganopolysiloxane and condensation-curing organopolysiloxane compositions which cure in the presence of an organotin compound or a titanate ester.

Addition reaction-curing organopolysiloxane compositions are preferred for their rapid curing rates and excellent uniformity of curing. A particularly preferred addition reaction-curing organopolysiloxane composition is prepared from:

(A) an organopolysiloxane having at least 2 lower alkenyl groups in each molecule;
(B) an organopolysiloxane having at, least 2 silicon-bonded hydrogen atoms in each molecule; and
(C) a platinum-type catalyst.

In one embodiment the composition includes an emulsifying crosslinked organopolysiloxane elastomer, a non-emulsifying crosslinked organopolysiloxane elastomer, or a mixture thereof. The term "non-emulsifying," as used herein, defines crosslinked organopolysiloxane elastomers from which polyoxyalkylene units are absent. The term "emulsifying," as used herein, means crosslinked organopolysiloxane elastomers having at least one polyoxyalkylene (e.g., polyoxyethylene or polyoxypropylene) unit. Preferred emulsifying elastomers herein include polyoxyalkylene modified elastomers formed from divinyl compounds, particularly siloxane polymers with at least two free vinyl groups, reacting with Si—H linkages on a polysiloxane backbone. Preferably, the elastomers are dimethyl polysiloxanes crosslinked by Si—H sites on a molecularly spherical MQ resin. Emulsifying crosslinked organopolysiloxane elastomers can notably be chosen from the crosslinked polymers described in U.S. Pat. Nos. 5,412,004, 5,837,793, and 5,811,487. An emulsifying elastomer comprising dimethicone copolyol crosspolymer (and) dimethicone is available from Shin Etsu under tradename KSG-21.

Advantageously, the non-emulsifying elastomers are dimethicone/vinyl dimethicone crosspolymers. Such dimethicone/vinyl dimethicone crosspolymers are supplied by a variety of suppliers including Dow Corning (DC 9040 and DC 9041), General Electric (SFE 839), Shin Etsu (KSG-15, 16, 18 [dimethicone/phenyl vinyl dimethicone crosspolymer]), and Grant Industries (GRANSIL™ line of elastomers). Cross-linked organopolysiloxane elastomers useful in the present invention and processes for making them are further described in U.S. Pat. No. 4,970,252, U.S. Pat. No. 5,760,116, and U.S. Pat. No. 5,654,362. Additional crosslinked organopolysiloxane elastomers useful in the present invention are disclosed in Japanese Patent Application JP 61-18708, assigned to Pola Kasei Kogyo KK.

Commercially available elastomers preferred for use herein are Dow Corning's 9040 silicone elastomer blend, Shin Etsu's KSG-21, and mixtures thereof.

4. Carrier for Silicone Elastomer

The topical compositions of the present invention include from about 1% to about 80%, by weight of the composition, of a suitable carrier for the for the crosslinked organopolysiloxane elastomer component described above. The carrier, when combined with the cross-linked organopolysiloxane elastomer particles of the present invention, serves to suspend and swell the elastomer particles to provide an elastic, gel-like network or matrix. The carrier for the cross-linked siloxane elastomer is liquid under ambient conditions, and preferably has a low viscosity to provide for improved spreading on skin.

Concentrations of the carrier in the cosmetic compositions of the present invention will vary primarily with the type and amount of carrier and the cross-linked siloxane elastomer employed. Preferred concentrations of the carrier are from about 5% to about 50%, more preferably from about 5% to about 40%, by weight of the composition.

The carrier for the cross-linked siloxane elastomer includes one or more liquid carriers suitable for topical application to human skin. These liquid carriers may be organic, silicone-containing or fluorine-containing, volatile or non-volatile, polar or non-polar, provided that the liquid carrier forms a solution or other homogenous liquid or liquid dispersion with the selected cross-linked siloxane elastomer at the selected siloxane elastomer concentration at a temperature of from about 28° C. to about 250° C., preferably from about 28° C. to about 100° C., preferably from about 28° C. to about 78° C. The term "volatile" as used herein refers to all materials that are not "non-volatile" as previously defined herein. The phrase "relatively polar" as used herein means more polar than another material in terms of solubility parameter; i.e., the higher the solubility parameter the more polar the liquid. The term "non-polar" typically means that the material has a solubility parameter below about 6.5 $(cal/cm^3)^{0.5}$.

5. Non-Polar, Volatile Oils

The non-polar, volatile oil tends to impart highly desirable aesthetic properties to the compositions of the present invention. Consequently, the non-polar, volatile oils are preferably utilized at a fairly high level. Non-polar, volatile oils particularly useful in the present invention are silicone oils; hydrocarbons; and mixtures thereof. Such non-polar, volatile oils are disclosed, for example, in Cosmetics, Science, and Technology, Vol. 1, 27-104 edited by Balsam and Sagarin, 1972. Examples of preferred non-polar, volatile hydrocarbons include polydecanes such as isododecane and isodecane (e.g., Permethyl-99A which is available from Presperse Inc.) and the C7-C8 through C12-C15 isoparaffins (such as the Isopar Series available from Exxon Chemicals). Particularly preferred volatile silicone oils are selected from cyclic volatile silicones with formula:

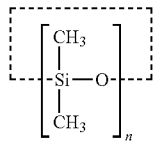

wherein n is from about 3 to about 7; and linear volatile silicones with formula:

$(CH_3)_3Si-O-[Si(CH_3)_2-O]_m-Si(CH_3)_3$ wherein m is from about 1 to about 7. Linear volatile silicones generally have a viscosity of less than about 5 centistokes at 25° C., whereas the cyclic silicones have viscosities of less than about 10 centistokes at 25° C. Highly preferred examples of volatile silicone oils include cyclomethicones of varying viscosities, e.g., Dow Corning 200, Dow Corning 244, Dow Corning 245, Dow Corning 344, and Dow Corning 345, (from Dow Corning Corp.); SF-1204 and SF-1202 Silicone Fluids (from G.E. Silicones), GE 7207 and 7158 (from General Electric Co.); and SWS-03314 (from SWS Silicones Corp.).

f. Relatively Polar, Non-Volatile Oils

The non-volatile oil is "relatively polar" as compared to the non-polar, volatile oil discussed above. Therefore, the non-volatile co-carrier is more polar (i.e., has a higher solubility parameter) than at least one of the non-polar, volatile oils. Relatively polar, non-volatile oils potentially useful in the present invention are disclosed, for example, in Cosmetics, Science, and Technology, Vol. 1, 27-104 edited by Balsam and Sagarin, 1972; U.S. Pat. Nos. 4,202,879 and 4,816,261. Relatively polar, non-volatile oils useful in the present invention include silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof.

6. Non-Polar, Non-Volatile Oils

In addition to the liquids discussed above, the carrier for the cross-linked siloxane elastomer may optionally include non-volatile, non-polar oils. Typical non-volatile, non-polar emollients are disclosed, for example, in Cosmetics, Science, and Technology, Vol. 1, 27-104 edited by Balsam and Sagarin, 1972; U.S. Pat. Nos. 4,202,879 and 4,816,261. The non-volatile oils useful in the present invention are essentially non-volatile polysiloxanes, paraffinic hydrocarbon oils, and mixtures thereof.

7. Dispersed Aqueous Phase

The topical compositions of the present invention comprise from about 30% to about 90%, more preferably from about 50% to about 85%, and even more preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention will typically comprise from about 25% to about 90%, preferably from about 40% to about 85%, more preferably from about 60% to about 80%, water in the dispersed aqueous phase by weight.

8. Emulsifier for Dispersing the Aqueous Phase

The water-in-silicone emulsions of the present invention preferably comprise an emulsifier. In one embodiment, the composition contains from about 0.1% to about 10% emulsifier, more preferably from about 0.2% to about 7.5%, even more preferably from about 0.5% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, non-silicon-containing emulsifiers, and mixtures thereof, known by those skilled in the art for use in topical personal care products. Preferably these emulsifiers have an HLB value of less than about 14, more preferably from about 2 to about 14, and even more preferably from about 4 to about 14. Emulsifiers having an HLB value outside of these ranges can be used in combination with other emulsifiers to achieve an effective weighted average HLB for the combination that falls within these ranges.

Silicone emulsifiers are preferred. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols.

Nonlimiting examples of dimethicone copolyols and other silicone surfactants useful as emulsifiers herein include polydimethylsiloxane polyether copolymers with pendant polyethylene oxide side chains, polydimethylsiloxane polyether copolymers with pendant polypropylene oxide side chains, polydimethylsiloxane polyether copolymers with pendant mixed polyethylene oxide and polypropylene oxide side chains, polydimethylsiloxane polyether copolymers with pendant mixed poly(ethylene)(propylene)oxide side chains, polydimethylsiloxane polyether copolymers with pendant organobetaine side chains, polydimethylsiloxane polyether copolymers with pendant carboxylate side chains, polydimethylsiloxane polyether copolymers with pendant quaternary ammonium side chains; and also further modifications of the preceding copolymers containing pendant C2-C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this latter material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate.

Among the non-silicone-containing emulsifiers useful herein are various non-ionic and anionic emulsifying agents such as sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, soaps, and mixtures thereof. Other suitable emulsifiers are described, for example, in McCutcheon's, Detergents and Emulsifiers, North American Edition (1986), published by Allured Publishing Corporation; U.S. Pat. Nos. 5,011,681, 4,421,769, and 3,755,560.

b. Oil-in-Water Emulsions

Other preferred topical carriers include oil-in-water emulsions, having a continuous aqueous phase and a hydrophobic, water-insoluble phase ("oil phase") dispersed therein. The "oil phase" can contain oil, silicone or mixtures thereof, and includes but is not limited to the oils and silicones described above in the section on water-in-oil emulsions. The distinction of whether the emulsion is characterized as an oil-in-water or silicone-in-water emulsions is a function of whether the oil phase is composed of primarily oil or silicone. The water phase of these emulsions consists primarily of water, but can also contain various other ingredients such as those water phase ingredients listed in the above section on water-in-oil emulsion. The preferred oil-in-water emulsions comprises from about 25% to about 98%, preferably from about 65% to about 95%, more preferably from about 70% to about 90% water by weight of the total composition.

In addition to a continuous water phase and dispersed oil or silicone phase, these oil-in-water compositions also comprise an emulsifier to stabilize the emulsion. Emulsifiers useful herein are well known in the art, and include non-ionic, anionic, cationic, and amphoteric emulsifiers. Nonlimiting examples of emulsifiers useful in the oil-in-water emulsions of this invention are given in McCutcheon's, Detergents and Emulsifiers, North American Edition (1986), published by Allured Publishing Corporation; U.S. Pat. No. 5,011,681; U.S. Pat. No. 4,421,769; and U.S. Pat. No. 3,755,560.

3. Additional Optional Ingredients

The compositions of the present invention may contain a variety of other ingredients that are conventionally used in given product types provided that they do not unacceptably alter the benefits of the invention. These ingredients should be included in a safe and effective amount for a personal care composition for application to skin.

The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, anti-foaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, fatty alcohols and fatty acids, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents, skin-conditioning agents, skin soothing and/or healing agents and derivatives, skin treating agents, thickeners, and vitamins and derivatives thereof. Additional non-limiting examples of additional suitable skin treatment actives are included in U.S. 2003/0082219 in Section I (i.e. hexamidine, zinc oxide, and niacinamide); U.S. Pat. No. 5,665,339 at Section D (i.e. coolants, skin conditioning agents, sunscreens and pigments, and medicaments); and US 2005/0019356 (i.e. desquamation actives, anti-acne actives, chelators, flavonoids, and antimicrobial and antifungal actives). Examples of suitable emulsifiers and surfactants can be found in, for example, U.S. Pat. No. 3,755,560, U.S. Pat. No. 4,421,769, and McCutcheon's Detergents and Emulsifiers, North American Edition, pages 317-324 (1986). It should be noted, however, that many materials may provide more than one benefit, or operate via more than one mode of action. Therefore, classifications herein are made for the sake of convenience and are not intended to limit the active to that particular application or applications listed. Some useful optional ingredients include:

a. Anti-Wrinkle Actives and/or Anti-Atrophy Actives

In another embodiment the composition comprises one or more anti-wrinkle actives or anti-atrophy actives. Exemplary anti-wrinkle/anti-atrophy actives suitable for use in the compositions of the present invention include hydroxy acids (e.g., salicylic acid, glycolic acid), keto acids (e.g., pyruvic acid), ascorbic acid (vitamin C), phytic acid, lysophosphatidic acid, flavonoids (e.g., isoflavones, flavones, etc.), stilbenes, cinnamates, resveratrol, kinetin, zeatin, dimethylaminoethanol, peptides from natural sources (e.g., soy peptides), salts of sugar acids (e.g., Mn gluconate), and retinoids which enhance the keratinous tissue appearance benefits of the present invention, especially in regulating keratinous tissue condition, e.g., skin condition, and other vitamin B compounds (e.g., thiamine (vitamin B1), pantothenic acid (vitamin B5), carnitine (vitamin Bt), riboflavin (vitamin B2), and their derivatives and salts (e.g., HCl or calcium salts)).

b. Anti-Oxidants and/or Racial Scavengers

In another embodiment the composition comprises an anti-oxidant/radical scavenger. The anti-oxidant/radical scavenger is especially useful for providing protection against UV radiation that can cause increased scaling or texture changes in the stratum corneum and against other environmental agents, which can cause skin damage. The anti-oxidant/radical scavenger may be from about 0.01% to about 10%, or from about 0.1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), amines (e.g., N,N-diethylhydroxylamine, amino-guanidine), nordihydroguaiaretic acid, bioflavonoids, amino acids silymarin, tea extracts, and grape skin/seed extracts may be used. Preferred anti-oxidants/radical scavengers are selected from esters of tocopherol, more preferably tocopherol acetate.

c. Anti-Inflammatory Agents

In another embodiment the composition comprises anti-inflammatory at from about 0.01% to about 10%, more preferably from about 0.5% to about 5%, of the composition. The anti-inflammatory agent enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency.

Steroidal anti-inflammatory agents, include but are not limited to, corticosteroids such as hydrocortisone. A second class of anti-inflammatory agents, which is useful in the compositions, includes the nonsteroidal anti-inflammatory agents. The varieties of compounds encompassed by this group are well known to those skilled in the art. Specific non-steroidal anti-inflammatory agents useful in the composition invention include, but are not limited to, salicylates, flufenamic acid, etofenamate, aspirin, and mixtures thereof.

Additional anti-inflammatory agents useful herein include allantoin and compounds of the Licorice (the plant genus/species *Glycyrrhiza glabra*) family, including glycyrrhetic acid, glycyrrhizic acid, and derivatives thereof (e.g., salts and esters).

d. Anti-Cellulite Agents

In another embodiment the composition comprises an anti-cellulite agent. Suitable agents may include, but are not limited to, xanthine compounds (e.g., caffeine, theophylline, theobromine, and aminophylline).

e. Tanning Actives

In another embodiment the composition comprises a tanning active. When present, it is preferable that the compositions comprise from about 0.1% to about 20%, more preferably from about 2% to about 7%, and even more preferably from about 3% to about 6%, by weight of the composition, of a tanning active. A preferred tanning active is dihydroxyacetone.

f. Skin Lightening Agents

The compositions of the present invention may comprise a skin lightening agent, at from about 0.1% to about 10%, more preferably from about 0.2% to about 5%, also preferably from about 0.5% to about 2%, by weight of the composition, of a skin lightening agent. Suitable skin lightening agents include those known in the art, including kojic acid, arbutin, tranexamic acid, ascorbic acid and derivatives thereof (e.g., magnesium ascorbyl phosphate or sodium ascorbyl phosphate, ascorbyl glucoside, and the like). Other skin lightening materials suitable for use herein include Acitwhite® (Cognis), Emblica® (Rona), Azeloglicina (Sinerga) and extracts (e.g. mulberry extract).

g. Sunscreen Actives

The compositions of the subject invention may optionally contain a sunscreen active at from about 1% to about 20%, more typically from about 2% to about 10% by weight of the composition. As used herein, "sunscreen active" includes both sunscreen agents and physical sunblocks. Suitable sunscreen actives may be organic or inorganic.

A wide variety of conventional sunscreen actives are suitable for use herein. Sagarin, et al., at Chapter VIII, pages 189 et seq., of Cosmetics Science and Technology (1972), discloses numerous suitable actives. Examples include 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone; octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-trimethylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, titanium dioxide, and mixtures of these compounds.

h. Conditioning Agents

The compositions of the present invention may comprise a conditioning agent selected from the group consisting of humectants, moisturizers, or skin conditioners, each can be present at a level of from about 0.01% to about 40%, more preferably from about 0.1% to about 30%, and even more preferably from about 0.5% to about 15% by weight of the composition. These materials include, but are not limited to, guanidine; urea; glycolic acid and glycolate salts (e.g. ammonium and quaternary alkyl ammonium); lactic acid and lactate salts (e.g., ammonium and quaternary alkyl ammonium); aloe vera in any of its variety of forms (e.g., aloe vera gel); polyhydroxy compounds such as sorbitol, mannitol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fructose, sucrose, etc.); hyaluronic acid; lactamide monoethanolamine; acetamide monoethanolamine; sucrose polyester; petrolatum; and mixtures thereof.

Suitable moisturizers, also referred to in the present invention as humectants, include urea, guanidine, glycolic acid and glycolate salts (e.g. ammonium and quaternary alkyl ammonium), lactic acid and lactate salts (e.g. ammonium and quaternary alkyl ammonium), aloe vera in any of its variety of forms (e.g. aloe vera gel), polyhydroxy alcohols (such as sorbitol, glycerol, hexanetriol, propylene glycol, hexylene glycol and the like), polyethylene glycol, sugars and starches, sugar and starch derivatives (e.g. alkoxylated glucose), hyaluronic acid, lactamide monoethanolamine, acetamide monoethanolamine, and mixtures thereof.

i. Thickening Agents (Including Thickeners and Gelling Agents)

The compositions of the present invention can comprise one or more thickening agents, preferably from about 0.05% to about 10%, more preferably from about 0.1% to about 5%, and even more preferably from about 0.25% to about 4%, by weight of the composition. Nonlimiting classes of thickening agents include those selected from the group consisting of: Carboxylic Acid Polymers (crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol); Crosslinked Polyacrylate Polymers (including both cationic and nonionic polymers, such as described in U.S. Pat. Nos. 5,100,660; 4,849,484; 4,835,206; 4,628,078; 4,599,379, and EP 228,868); Polymeric sulfonic acid (such as copolymers of acryloyldimethyltaurate and vinylpyrrolidone) and hydrophobically modified polymeric sulfonic acid (such as crosspolymers of acryloyldimethyltaurate and beheneth-25 methacrylate); Polyacrylamide Polymers (such as nonionic polyacrylamide polymers including substituted branched or unbranched polymers such as polyacrylamide and isoparaffin and laureth-7 and multi-block copolymers of acrylamides and substituted acrylamides with acrylic acids and substituted acrylic acids); Polysaccharides (nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof); Gums (i.e. gum agents such as acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof); and crystalline, hydroxyl-containing fatty acids, fatty esters or fatty waxes (such as microfibrous bacterial cellulose structurants as disclosed in U.S. Pat. No. 6,967,027 to Heux et al.; U.S. Pat. No. 5,207,826 to Westland et al.; U.S. Pat. No. 4,487,634 to Turbak et al.; U.S. Pat. No. 4,373,702 to Turbak et al. and U.S. Pat. No. 4,863,565 to Johnson et al., U.S. Pat. Publ. No. 2007/0027108 to Yang et al.)

j. Water-Soluble Vitamins

The compositions of the present invention may contain a safe and effective amount of one or more water-soluble vitamins. Examples of water-soluble vitamins include, but are not limited to, water-soluble versions of vitamin B, vitamin B derivatives, vitamin C, vitamin C derivatives, vitamin K, vitamin K derivatives, vitamin D, vitamin D derivatives, vitamin E, vitamin E derivatives, and mixtures thereof. The vitamin compounds may be included as the substantially pure material, or as an extract obtained by suitable physical and/or chemical isolation from natural (e.g., plant) sources. When vitamin compounds are present in the compositions of the instant invention, the compositions preferably contain from about 0.0001% to about 50%, more preferably from about 0.001% to about 10%, still more preferably from about 0.01% to about 5%, and still more preferably from about 0.1% to about 5%, by weight of the composition, of the vitamin compound.

k. Particulate Material

The compositions of the present invention may contain one or more particulate materials. Nonlimiting examples of particulate materials useful in the present invention include colored and uncolored pigments, interference pigments, inorganic powders, organic powders, composite powders, optical brightener particles, and combinations thereof. These particulates can be platelet shaped, spherical, elongated or needle-shaped, or irregularly shaped, surface coated or uncoated, porous or non-porous, charged or uncharged, and can be added to the current compositions as a powder or as a pre-dispersion. These particulate materials may provide a wide range of functions, including but not limited to modifying skin feel, masking the appearance of certain skin characteristics such as exfoliating benefits, blotchy areas, age spots, freckles, fine lines, wrinkles, and pores, absorbing excess skin sebum/oils, reducing skin shine, improving application properties of the composition, masking the color of other components of the composition, filling in skin pores, lines and wrinkles, and reducing migration of liquid materials on the skin. Preferably, particulate materials are present in the composition in levels of from about 0.01% to about 20%, more preferably from about 0.05% to about 10%, still more preferably from about 0.1% to about 5%, by weight of the composition. There are no specific limitations as to the pigment, colorant or filler powders used in the composition. Examples of suitable particulates for use herein are described in U.S. Patent Publ. 2005/0019356A1.

4. Composition Forms

The topical compositions of the subject invention, including but not limited to lotions, milks, mousses, serums, sprays, aerosols, foams, sticks, pencils, gels, creams and ointments, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients is known and may be used herein. Sagarin, Cosmetics, Science and Technology, 2nd Ed, v1, pp. 32-43 (1972), contains numerous examples of materials suitable as an emollient. Non-limiting examples of preferred emollients include glycerin and fatty acid esters. The emollient can be used in an amount of from about 0.001 to about 20%, or from about 0.01 to about 15%, or from about 0.1 to about 10% by weight of the composition.

The physical form of the cleansing compositions is not critical. The compositions can be, for example, formulated as toilet bars, liquids, shampoos, bath gels, hair conditioners, hair tonics, pastes, or mousses. Toilet bars are preferred since this is the form of cleansing agent most commonly used to wash the skin. Rinse-off cleansing compositions, such as shampoos, require a delivery system adequate to deposit sufficient levels of actives on the skin and scalp. A preferred delivery system involves the use of insoluble complexes. See U.S. Pat. No. 4,835,148.

The compositions of the present invention may also be in the form of cosmetics. Suitable cosmetic forms include, but are not limited to, foundations, lipsticks, rouges, mascaras, and the like. Such cosmetic products may include conventional ingredients such as oils, colorants, pigments, emollients, fragrances, waxes, stabilizers, and the like. Exemplary carriers and other ingredients which are suitable for use herein are described in U.S. Pat. No. 6,060,547.

5. Optional Lathering Surfactants

Where the personal care composition is a wash or cleansing composition, the carrier can comprise one or more lathering surfactants and the carrier can be at a level of from about 60% to about 99.99%. A lathering surfactant defined herein as surfactant, which when combined with water and mechanically agitated generates a foam or lather. Preferably, these surfactants or combinations of surfactants should be mild, which means that these surfactants provide sufficient cleansing or detersive benefits but do not overly dry the skin or hair while still lathering. Those of skill in the art should understand that the lathering surfactant is in addition to the surfactant derived from a predominantly unsaturated triglyceride described above.

A wide variety of lathering surfactants are useful herein and include those selected from the group consisting of anionic lathering surfactants, nonionic lather surfactants, amphoteric lathering surfactants, and mixtures thereof. Generally, the lathering surfactants are fairly water soluble. When used in the composition, at least about 4% of the lathering surfactants have a HLB value greater than about ten. Examples of such surfactants are found in and U.S. Pat. No. 5,624,666. Cationic surfactants can also be used as optional components, provided they do not negatively impact the overall lathering characteristics of the required lathering surfactants Concentrations of these surfactant are from about 10% to about 20%, alternatively from about 6% to about 25%, and alternatively from about 4% to about 30% by weight of the composition. To avoid skin irritation issues, the compositions should have a ratio by weight of the composition of anionic surfactant to amphoteric and/or zwitterionic surfactant is from about 1.1:1 to about 1:1.5, alternatively from about 1.25:1 to about 1:2, and alternatively from about 1.5:1 to about 1:3.

Anionic lathering surfactants useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929,678. A wide variety of anionic lathering surfactants are useful herein. Non-limiting examples of anionic lathering surfactants include those selected from the group consisting of sarcosinates, sulfates, sulfonates, isethionates, taurates, phosphates, lactylates, glutamates, and mixtures thereof.

Other anionic materials useful herein are soaps (i.e., alkali metal salts, e.g., sodium or potassium salts) of fatty acids, typically having from about 8 to about 24 carbon atoms, preferably from about 10 to about 20 carbon atoms, monoalkyl, dialkyl, and trialkylphosphate salts, alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and alkanolamine (e.g., triethanolamine). Also useful are taurates which are based on taurine, which is also known as 2-aminoethanesulfonic acid, and glutamates, especially those having carbon chains between $C_8$ and $C_{16}$.

Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Suitable amphoteric or zwitterionic detersive surfactants for use in the compositions herein include those which are known for use in hair care or other personal care cleansing. Concentration of such amphoteric detersive surfactants is from about 1% to about 10%, alternatively from about 0.5% to about 20% by weight of the composition. Non-limiting examples of suitable zwitterionic or amphoteric surfactants are described in U.S. Pat. No. 5,104,646 and U.S. Pat. No. 5,106,609.

Nonionic lathering surfactants for use in the compositions of the present invention are disclosed in McCutcheon's, Detergents and Emulsifiers, North American edition (1986), published by allured Publishing Corporation; and McCutcheon's, Functional Materials, North American Edition (1992); both of which are incorporated by reference herein in their entirety. Nonionic lathering surfactants useful herein include those selected from the group consisting of alkyl glucosides, alkyl polyglucosides, polyhydroxy fatty acid amides, alkoxylated fatty acid esters, lathering sucrose esters, amine oxides, and mixtures thereof.

Other examples of nonionic surfactants include amine oxides. Amine oxides correspond to the general formula $R^1R^2R^3NO$, wherein $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals. Examples of amine oxides suitable for use in this invention include dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide; 2-dodecoxyethyldimethylamine oxide, 3-dodecoxy-2-hydroxypropyldi(3-hydroxypropyl)amine oxide, dimethylhexadecylamine oxide.

Preferred lathering surfactants for use herein are the following, wherein the anionic lathering surfactant is selected from the group consisting of ammonium lauroyl sarcosinate, sodium trideceth sulfate, sodium lauroyl sarcosinate, sodium myristoyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium lauroyl lactylate, triethanolamine lauroyl lactylate, and mixtures thereof; wherein the nonionic lathering surfactant is selected from the group consisting of lauramine oxide, cocoamine oxide, decyl polyglucose, lauryl polyglucose, sucrose cocoate, $C_{12-14}$ glucosamides, sucrose laurate, and mixtures thereof; and wherein the amphoteric lathering surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

6. Methods of Use

The personal care composition can be in any suitable personal care composition which comes in contact with skin or hair. Non-limiting examples of suitable personal care compositions include cosmetics, moisturizers, lotions, oils, personal cleansers, facial cleansers, shave gels, shave foams, shave oils, after shaves, pre-shave treatments such as lotions, and so forth. The present composition can be used in combination with various hair removal applications (prior to, concurrently with, and/or after), including but not limited to shaving (wet or dry shaving, via electric razors, via powered or manual razors which can be reusable or disposable, and combinations thereof), epilation, electrolysis, wax or depilatories as well as energy delivery devices to help regulate hair growth. Nonlimiting examples of energy deliver devices include: light, heat, sound (including ultrasonic waves and radio frequency), electrical energy, magnetic energy, electromagnetic energy (including radiofrequency waves and microwaves), and combinations thereof. The light energy may be delivered by devices including, but not limited to, lasers, diode lasers, diode laser bars, diode laser arrays, flash lamps, intense pulsed light (IPL) sources, and combinations thereof. See e.g. US2006/0235370A1.

In one preferred embodiment, the personal care composition is used as a post shave moisturizers and/or balms. The present invention also relates to a method of reducing irritation by down regulating cytokine activity by applying a personal care composition of the present invention onto skin to form a treated surface. Where the composition is used in a shaving regimen, the method of use can further comprise a step of shaving a portion of skin which can be performed before or after applying the composition to skin. In one preferred embodiment, the personal care composition is used in a post-shave application such as a leave-on gels, balm, or moisturizer to be applied to skin immediately after or shortly after shaving. Those of skill in the art will understand that the hair removal step can be shaving or any of the hair removal technologies described in the previous paragraph.

In another embodiment, the invention comprises a step of leaving said personal care composition on said portion of treated skin for from about 5 seconds to 120 seconds, alternatively from about 10 seconds to about 60 seconds, alternatively from about 30 seconds to about 45 seconds. In one embodiment, the composition is left on for at least 2 seconds prior to being removed either by a razor, being washed off or otherwise washed away. Without intending to be bound by theory, it is believed that leaving said personal care composition on skin for such a period of time allows the multi-active system to down regulate cytokine activity as desired.

In another embodiment, the invention further comprises a step of at least partially removing said personal care composition from said portion of treated skin, followed by applying a second personal care composition comprising a multi-active system (which can be in the same relative proportions as used in the earlier personal care composition or at different proportions), wherein the multi-active system is at a level which is greater than the level in said personal care composition already on the skin. The removal step can be by washing off, removing while shaving or otherwise removing hairs, or wiping off with a substrate such as a towel. Where multiple personal care compositions are used, each comprising the multi-active system of the present invention, the level of the multi-active system in each subsequent composition is at least the same, preferably increasing by about 10%, or about 20%, or about 50%, or about 100% by weight of the level of multi-active system in the previously applied composition. In one embodiment, the personal care composition can be a facial scrub or cleanser and the second personal care composition can be a shaving preparation, such as shaving bars, aerosol or non-aerosol shaving foams or gels, or a post foaming gel. In another embodiment, the personal care composition can be any of the compositions mentioned previously, the step of at least partially removing the composition can be done while shaving, and the second personal care composition can be a balm, moisturizer or skin care lotion. Without intending to be bound by theory, it is believed that by increasing the level of multi-active system in subsequent compositions that the down regulation cytokine activity continues to be felt by the user. Such a regimen can be particularly useful for consumers who have sensitive skin and desire anti-irritation products.

7. In Vitro Assay Testing

The following in vitro assay test was conducted to determine the effect of Olivem and SymRelief on cytokine expression in hTERT keratinocytes:

Background: hTERT-keratinocytes are a telomerase-immortalized neonatal Caucasian epidermal keratinocyte line. Cell culture of this type are well known in the literature and have been used as models for multiple pathways as shown in the following references: Shay and Wright; Carcinogenesis, vol 26; no 5, pp 867-874, 2005; Bodner, et. al., Science, vol 279 pp 349-352, 1998; Ramirez, et. al., Oncogene, 22; pp 433-444, 2002. These cells display many features characteristic of normal primary keratinocytes and respond to normal growth controls in vitro.

Treatments—all Measures were Run in Triplicate.

To ensure proper levels of the biological active molecules for the in vitro study, dilution studies were conducted and ATP was analyzed for the highest non-cytotoxic concentration. Olivem 460 (lot LG0833 from B&T, Milan Italy) at a level of 0.000156% and SymRelief (from Symrise) at a level of 0.0625% were determined to be appropriate respective concentrations for this study. ATP analysis is described below.

ATP analysis was conducted using Cell Titer-Glo. The CellTiter-Glo Luminescent Cell Viability Assay was obtained from Promega Corporation (Madison, Wis.). This assay is a homogeneous method for determining the number of viable cells in culture based on quantitation of ATP present, signaling the presence of metabolically active cells. After the final treatment and supernatants collected, the CellTiter-Glo reagent was added. The reagent was then transferred to a BD Falcon (Franklin Lakes, N.J.) Microtest 96-well Assay Plate (black, flat bottom, reference 353945, lot 041151). Luminescence was read on a Perkin Elmer Fluorimeter (Wallac Envision 2101 Multilabel Reader). Relative luminescence units were plotted in percent control versus treatment concentration.

hTERT cells were cultured in complete EpiLife (Cascade Biologics, Portland, Oreg.) culture media in T75 culture flasks (Falcon, Becton Dickinson Labware, Franklin Lakes, N.J.) under 37° C./5% $CO_2$ conditions. When the flasks reached 60-80% confluence, the cells were removed from the flasks with mild enzymatic treatment according to the manufacturer's suggestions (Cascade Biologics), washed and resuspended in EpiLife Culture Medium at a concentration of $10^5$/ml. 2 ml of the cell suspension (density 20,000/cm$^2$) were plated in each well of a 6-well culture dish (Falcon) and cultured under 37° C./5% $CO_2$ conditions overnight. A complete media exchange was performed and the cells were again cultured overnight under 37° C./5% $CO_2$ conditions. The culture media was removed and 2 ml of treatment were placed in each well (n=3/treatment) and the cells were cultured overnight (18 hrs). After the treatment period, the treatments were removed and replaced with fresh EpiLife culture Media.

The cells were cultured overnight under 37° C./5% $CO_2$ conditions. At the end of the treatment, the cell culture supernatants were collected and analyzed immediately for Interleukin-8 with an R&D Systems (Minneapolis, Minn.) kit which deploys the quantitative sandwich immunoassay technique. ATP was measured from cell lysates an indicator of viability. IL-8 was indexed to cell viability to ensure a proper reading of actual activity.

As shown in the Table A below, the combination of Olivem 460 and SymRelief exhibit synergistic activity reducing IL-8 (irritation marker) relative to the Olivem 460 and SymRelief materials alone.

TABLE A

| Active Ingredient | IL-8 | Stdev | Δ IL-8 vs control |
|---|---|---|---|
| Control - No Active | 32 | 4.4 | NA |
| Olivem 460 | 30 | 5.0 | −6.6% |
| SymRelief | 37 | 7.1 | 15% |
| Olivem 460 + SymRelief | 17(S) | 0.24 | −47%(S) |

(S) - significant at >95% confidence

Applicants have found that when a combination of both Olivem 460 and Symrelief are used in combination, the resultant decrease in cytokine levels is demonstrated by a decrease in IL-8 measurements. Note that the ΔIL-8 vs. control is calculated as the % difference in IL-8 value versus the control. Applicants believe that the reduction in IL-8 levels from the combination of Olivem 460 and Symrelief will lead to a reduction in shave-induced irritation.

8. Examples

Example Set A

Moisturizer/Balm Making Instructions

Phase A materials are combined and heated in a container. Phase B materials are combined and heated in a separate container. Phase B is added to Phase A under high shear. The mixture of Phases A and B is cooled and the contents of Phase C are added with mixing. Phase D materials are blended in a separate container and added to the mixture of Phases A, B, and C. The final mixture is stirred until well blended. Qs means quantity sufficient to reach 100%.

|  | Sample 1 | Sample 2 | Sample 3 | Sample 4 | Sample 5 | Sample 6 |
|---|---|---|---|---|---|---|
| Phase A | | | | | | |
| Water | Qs | Qs | Qs | Qs | Qs | Qs |
| Glycerin | 8.0000% | 6.0000% | 6.0000% | 6.0000% | 4.0000% | 5.0000% |
| Sorbitol | | | | | 2.0000% | 2.0000% |
| Disodium EDTA | 0.1000% | 0.1000% | 0.1000% | 0.1000% | 0.1000% | 0.1000% |
| Phase B | | | | | | |
| Cetearyl Alcohol | | | | | | |
| Emulgade Pl 68/50[1] | 0.2000% | 0.2000% | 0.2000% | 0.2000% | 0.2000% | 0.2000% |
| Cetiol SN[2] | 5.0000% | 5.0000% | 5.0000% | 3.5000% | 3.5000% | 5.0000% |
| Cetyl Alcohol | 0.8900% | 0.8900% | 0.8900% | 0.8900% | 0.8900% | 0.8900% |
| PEG-100 Stearate | 0.1000% | 0.1000% | 0.1000% | | 0.1000% | 0.1000% |
| Polymethylsilsesquioxane | 1.0000% | | 1.0000% | 1.0000% | 1.0000% | |
| Sorbitan Stearate | 0.1000% | 0.1000% | 0.1000% | 0.1000% | 0.1000% | 0.1000% |
| Steareth-2 | 0.1000% | 0.1000% | | | | |
| Steareth-21 | 0.1000% | 0.1000% | | | | |

-continued

| | | | | | | |
|---|---|---|---|---|---|---|
| Stearic acid | 0.1000% | 0.1000% | 0.1000% | | 0.1000% | 0.1000% |
| Stearyl Alcohol | 0.6100% | 0.6100% | 0.6100% | 0.6100% | 0.6100% | 0.6100% |
| Phase C | | | | | | |
| Aluminum Starch Octenylsuccinate | 4.0000% | 4.0000% | 4.0000% | 4.0000% | 3.0000% | 3.0000% |
| Aristoflex AVC[3] | 0.7500% | | 0.7500% | 0.7500% | 0.7500% | 0.7500% |
| Cyclomethicone | | | | | | |
| Dow Corning 1503[4] | 2.0000% | 2.0000% | 2.0000% | 2.0000% | 2.0000% | 2.0000% |
| FD&C Blue No. 1 (CI 42090) | 0.0002% | 0.0002% | 0.0002% | 0.0002% | 0.0002% | 0.0002% |
| Mackstat DM[5] | 0.0800% | 0.0800% | 0.0800% | 0.0800% | 0.0800% | 0.0800% |
| Glydant Plus Liquid[6] | 0.3200% | 0.3200% | 0.3200% | 0.3200% | 0.3200% | 0.3200% |
| KTZ Interfine Gold[7] | 0.1000% | 0.1000% | 0.1000% | 0.1000% | 0.1000% | 0.1000% |
| KTZ Interfine Green[8] | 0.5000% | 0.5000% | 0.5000% | 0.5000% | 0.2500% | 0.2500% |
| Olivem 460[9] | 0.2500% | 0.0833% | 0.2500% | 0.2500% | 0.2500% | 0.2500% |
| Sepiplus 400[10] | | 0.7500% | | | | |
| Symrelief[11] | 0.2500% | 0.2000% | 0.2500% | 0.2500% | 0.2000% | 0.2500% |
| Phase D | | | | | | |
| Fragrance | 0.8000% | 0.8000% | 0.8000% | 0.8000% | 0.8000% | 0.8000% |
| Menthol | 0.0500% | 0.0900% | 0.0900% | 0.0900% | 0.0500% | 0.0900% |
| Menthyl Lactate | 0.1500% | 0.2000% | 0.2000% | 0.2000% | 0.2500% | 0.2000% |

| | Sample 7 | Sample 8 | Sample 9 | Sample 10 | Sample 11 | Sample 12 |
|---|---|---|---|---|---|---|
| Phase A | | | | | | |
| Water | Qs | Qs | Qs | Qs | Qs | Qs |
| Glycerin | 4.0000% | 4.0000% | 2.0000% | 2.0000% | 3.0000% | 2.0000% |
| Sorbitol | | | 2.0000% | 2.0000% | 2.0000% | 2.0000% |
| Disodium EDTA | 0.1000% | 0.1000% | 0.0500% | 0.0500% | 0.0500% | 0.0500% |
| Phase B | | | | | | |
| Cetearyl Alcohol | | | 1.0000% | 1.0000% | 1.0000% | 1.0000% |
| Emulgade Pl 68/50[1] | 0.2000% | 0.2000% | | | | |
| Cetiol SN[2] | 5.0000% | 5.0000% | 1.5000% | 1.5000% | 1.5000% | 3.5000% |
| Cetyl Alcohol | 0.8900% | 0.8900% | | | | |
| PEG-100 Stearate | 0.1000% | | | | | |
| Polymethylsilsesquioxane | 1.0000% | 1.0000% | | | 1.0000% | 1.0000% |
| Sorbitan Stearate | 0.1000% | 0.1000% | | | | |
| Steareth-2 | | | 1.8000% | 1.8000% | 1.8000% | 1.8000% |
| Steareth-21 | | | 0.9000% | 0.9000% | 0.9000% | 0.9000% |
| Stearic acid | 0.1000% | | | | | |
| Stearyl Alcohol | 0.6100% | 0.6100% | | | | |
| Phase C | | | | | | |
| Aluminum Starch Octenylsuccinate | 3.0000% | 3.0000% | | | | |
| Aristoflex AVC[3] | 0.7500% | | 0.7500% | | | |
| Cyclomethicone | | | 2.0000% | 2.0000% | | |
| Dow Corning 1503[4] | 2.0000% | 2.0000% | 0.5000% | 0.5000% | 0.5000% | 0.5000% |
| FD&C Blue No. 1 (CI 42090) | 0.0002% | 0.0002% | 0.0002% | 0.0002% | 0.0002% | 0.0002% |
| Mackstat DM[5] | 0.0800% | 0.0800% | 0.0800% | 0.0800% | 0.0800% | 0.0800% |
| Glydant Plus Liquid[6] | 0.3200% | 0.3200% | 0.3200% | 0.3200% | 0.3200% | 0.3200% |
| KTZ Interfine Gold[7] | 0.1000% | 0.1000% | | | 0.1000% | |
| KTZ Interfine Green[8] | 0.5000% | 0.5000% | | | 0.2500% | |
| Olivem 460[9] | 0.2500% | 0.3300% | 0.1000% | 0.1000% | 0.2500% | 0.2500% |
| Sepiplus 400[10] | | 0.7500% | | 1.0000% | 1.0000% | 0.7500% |
| Symrelief[11] | 0.2500% | 0.2000% | 0.2000% | 0.2000% | 0.2500% | 0.2500% |
| Phase D | | | | | | |
| Fragrance | 0.8000% | 0.8000% | 0.4000% | 0.4000% | 0.4000% | 0.4000% |
| Menthol | 0.0900% | 0.0500% | | | 0.0500% | 0.0500% |
| Menthyl Lactate | 0.2000% | 0.1500% | | | 0.1500% | 0.1500% |

[1] Cetearyl Glucoside (and) Cetearyl Alcohol from Cognis Corp, Cincinnati, OH
[2] Cetearyl Isononanoate from Cognis Corp, Cincinnati, OH
[3] Ammonium Acryloyldimethyltaurate/VP Copolymer from Clariant International AG, Switzerland.
[4] Dimethicone (and) Dimethiconol from Dow Corning, Midland, MI
[5] DMDM Hydantoin (and) Water from Rhodia Inc, Cranbury. NJ
[6] DMDM Hydantoin (and) Iodopropynyl Butylcarbamate (and) Water from Lonza Group Ltd, Switzerland
[7] Mica (and) Titanium dioxide (and) Tin Oxide from Kobo Products, Plainfield, NJ
[8] Mica (and) Titanium dioxide from Kobo Products, Plainfield, NJ
[9] Sodium PEG-7 Olive Oil Carboxylate from B&T Company, Milan, Italy
[10] Polyacrylate-13 (and) Polyisobutene (and) Polysorbate 20 from Seppic Inc, Fairfield, NJ
[11] Bisabolol (and) Zingiber Officinale Root Extract from Symrise Inc, Teterboro, NJ Example Set B Washing Compositions

| Ingredient | Sample 1 | Sample 2 | Sample 3 | Sample 4 | Sample 5 |
|---|---|---|---|---|---|
| Water | Qs | Qs | Qs | Qs | Qs |
| Polyquaternium-10 (JR-400) | 0.25 | 0.25 | 0.25 | 0.25 | 0.25 |
| Disodium EDTA | 0.10 | 0.10 | 0.10 | 0.10 | 0.10 |
| PEG-100 | 0.20 | 0.20 | 0.20 | 0.20 | 0.20 |
| Sorbitol[13] | 1.99 | 1.99 | 1.99 | 1.99 | 1.99 |
| Glycerin | 1.99 | 1.99 | 1.99 | 1.99 | 1.99 |
| Sodium Lauroamphoacetate[14] | 3.19 | 3.19 | 3.19 | 3.19 | 3.19 |
| Sodium Trideceth Sulfate[15] | 3.24 | 3.24 | 3.24 | 3.24 | 3.24 |
| Sodium Myristol Sarcosinate[16] | 1.49 | 1.49 | 1.49 | 1.49 | 1.49 |
| Lauric Acid | 0.15 | 0.15 | 0.15 | 0.15 | 0.15 |
| Citric Acid | 0.50 | 0.50 | 0.50 | 0.50 | 0.50 |
| PEG-200 Hydrogenated Glyceryl Palmitate/PEG-7 Glyceryl Cocoate[17] | 2.99 | 2.99 | 2.99 | 2.99 | 2.99 |
| DMDM Hydantoin + Iodopropynyl Butalcarbamate | 0.40 | 0.40 | 0.40 | 0.40 | 0.40 |
| Perfume | 0.50 | 0.50 | 0.50 | 0.50 | 0.50 |
| Symrelief[9] | 0.11% | 0.073% | 0.11% | 0.073% | 0.27% |
| Olivem460[11] | 0.012% | 0.001% | 0.012% | 0.001% | 0.058% |
| Menthol | 0.00 | 0.10 | 0.10 | 0.08 | 0.04 |

[13]Sorbitol 70% Solution
[14]Sodium Lauroamphoacetate 32% Solution
[15]Sodium Trideceth Sulfate 65% Solution
[16]Sodium Myristol Sarcosinate 30% Solution
[17]Antil 200 - (Evonik/Goldschmidt)

Making Instructions for Washing Composition

Weigh out the water in a vessel sufficient to hold the entire batch. Insert an overhead mixer with impeller into the vessel and increase agitation to create a vortex. Sprinkle the polymer into the vortex, ensure well dissolved. Heat batch to about 60° C. to hydrate the polymer. Add EDTA, PEGs, Sorbitol, Glycerin, Sodium Lauroamphoacetate, and the surfactants while heating. After batch is at 60° C., add the lauric acid. Continue mixing at 60° C. for at least five minutes. Adjust to a pH from 5.9-6.5 with citric acid and/or water. Remove heat, allow to cool to 35° C. Once below 35° C., add the Symrelief, Olivem, perfume, preservatives and other ingredients.

Example Set C

Pre-Shave Prep Examples

The pre-shave prep samples above are made according to the method below.

Weigh out the water in a vessel sufficient to hold the entire batch. Insert an overhead mixer with impeller into the vessel and increase agitation to create a vortex. Pre-blend the thickener and polymer powders. Sprinkle the polymer blend into the vortex until incorporated. Begin heating batch to 70 C to hydrate the polymers. Once the batch is at 70 C, add the oil and mix until uniform and dispersed. Add the liquid dispersion polymer to the batch and mix until uniform and hydrated, increasing rpms to maintain good mixing. Add the surfactant and mix until uniform and dispersed. Begin cooling batch to below 45 C. Once below 45 C, add the Symrelief, Olivem, perfume, preservatives and other temperature-sensitive additives. Cool to below 35 C and QS with water

| Ingredient | Sample 1 | Sample 2 | Sample 3 | Sample 4 | Sample 5 |
|---|---|---|---|---|---|
| Water | Qs | Qs | Qs | Qs | Qs |
| Sepigel 305 (Polyacrylamide & C13-14 Isoparaffin & Laureth-7) | 2.00 | 2.00 | 2.00 | 2.00 | 2.00 |
| Polyox N12K (PEG-23M) | 0.50 | 0.50 | 0.50 | 0.50 | 0.50 |
| Natrosol 250 HHR (HEC) | 0.80 | 0.80 | 0.80 | 0.80 | 0.80 |
| Glycerin 99.7% Usp/Fcc | 5.00 | 5.00 | 5.00 | 5.00 | 5.00 |
| Brij 35 (Laureth-23) | 2.00 | 2.00 | 2.00 | 2.00 | 2.00 |
| Disodium EDTA | 0.10 | 0.10 | 0.10 | 0.10 | 0.10 |
| Perfume | 0.15 | 0.15 | 0.15 | 0.15 | 0.15 |
| Glydant Plus | 0.20 | 0.20 | 0.20 | 0.20 | 0.20 |
| Symrelief[11] | 0.11% | 0.073% | 0.11% | 0.073% | 0.27% |
| Olivem460[9] | 0.012% | 0.001% | 0.012% | 0.001% | 0.058% |
| Menthol | 0.00 | 0.05 | 0.05 | 0.04 | 0.02 |

Example Set D

Post Foaming Shave Gel Examples

Making instructions can be found in US 2006/0257349, paragraph 21. Note, Olivem and Symrelief are to be added the same time as the fragrance

| Ingredient | Sample 1 | Sample 2 | Sample 3 | Sample 4 | Sample 5 |
| --- | --- | --- | --- | --- | --- |
| Sorbitol 70% Solution | 0.97% | 0.97% | 0.97% | 0.97% | 0.97% |
| Glycerin | 0.49% | | 0.49% | | 0.49% |
| Water | QS | QS | QS | QS | QS |
| hydroxyethyl cellulose[18] | 0.49% | 0.49% | 0.49% | 0.49% | 0.49% |
| PEG-90M[19] | 0.06% | 0.06% | 0.06% | 0.06% | 0.06% |
| PEG-23M[20] | 0.05% | 0.05% | 0.05% | 0.05% | 0.05% |
| PTFE[21] | 0.15% | 0.15% | 0.15% | 0.15% | 0.15% |
| Palmitic acid | 7.53% | 7.53% | 7.53% | 7.53% | 7.53% |
| Stearic Acid | 2.53% | 2.53% | 2.53% | 2.53% | 2.53% |
| Glyceryl Oleate | 1.94% | 1.94% | 1.94% | 1.94% | 1.94% |
| Triethanolamine (99%) | 5.88% | 5.88% | 5.88% | 5.88% | 5.88% |
| Lubrajel Oil[22] | 0.49% | 0.97% | 0.49% | 0.97% | 0.49% |
| Symrelief[11] | 0.11% | 0.073% | 0.11% | 0.073% | 0.27% |
| Olivem460[9] | 0.012% | 0.001% | 0.012% | 0.001% | 0.058% |
| Menthol | | 0.11% | | 0.11% | |
| Fragrance | 0.87% | 0.87% | 0.87% | 0.87% | 0.87% |
| Other (e.g. Vit E, Aloe, etc.) | 0.10% | 0.10% | 0.10% | 0.10% | 0.10% |
| Dye | 0.10% | 0.10% | 0.10% | 0.10% | 0.10% |
| Isopentane (and) Isobutane | 2.8500% | 2.8500% | 2.8500% | 2.8500% | 2.8500% |

[18] Available as Natrosol 250 HHR from Hercules Inc., Wilmington, DE
[19] Available as Polyox WSR-301 from Amerchol Corp., Piscataway, NJ
[20] Available as Polyox WSR N-12K from Amerchol Corp., Piscataway, NJ
[21] Available as Microslip 519 from Micro Powders Inc., Tarrytown, NY
[22] Available from Guardian Laboratories, Hauppauge, NY All percentages and ratios used herein are by weight of the total composition and all measurements made are at 25° C., unless otherwise designated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Dermatologically acceptable," as used herein, means that the compositions or components described are suitable for use in contact with human keratinous tissue without undue toxicity, incompatibility, instability, allergic response, and the like.

All percentages disclosed herein, unless otherwise stated, are by weight of the named material itself that is found in the compositions, thereby excluding for example the weight associated with carriers, impurities and by-products found in the raw material.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All parts, ratios, and percentages herein, in the Specification, Examples, and Claims, are by weight and all numerical limits are used with the normal degree of accuracy afforded by the art, unless otherwise specified. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the DETAILED DESCRIPTION OF THE INVENTION are, in the relevant part, incorporated herein by reference; the citation of any document is not to be construed as an admission that it is prior art with respect to the present invention. To the extent that any meaning or definition of a term or in this written document conflicts with any meaning or definition in a document incorporated by reference, the meaning or definition assigned to the term in this written document shall govern.

Except as otherwise noted, the articles "a," "an," and "the" mean "one or more."

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
    a) from about 0.001% to about 10% of a multi-active system for down regulating cytokines, said multi active system comprising:
        i) bis-abolol and ginger extract, and
        ii) from about 0.01% to about 5% surfactant derived from a predominately unsaturated triglyceride comprising a sodium polyethylene glycol 7 olive oil carboxylate; and
    b) from about 50% to about 99.99% of a carrier.

2. The personal care composition of claim 1, wherein the level of bis-abolol and ginger extract is from about 0.01% to about 5%.

3. The personal care composition of claim 1, wherein the level of sodium polyethylene glycol 7 olive oil carboxylate is from about 0.1% to about 1%.

4. The personal care composition of claim 1, wherein the carrier is selected from the group consisting of an oil-in-water emulsion and a water-in-oil emulsion.

5. The personal care composition of claim 1, wherein the carrier is selected from a silicone-in-water emulsion and a water-in-silicone emulsion.

6. The personal care composition of claim 5, wherein the silicone comprises at least one of a silicone elastomer, a polyorganosiloxane oil, and a mixture thereof.

7. The personal care composition of claim 4, wherein the carrier further comprises at least one lipid or oil which is derived from animals, plants, or petroleum.

8. The personal care composition of claim 4, wherein the carrier further comprises an emulsifier.

9. The personal care composition of claim 1, further comprising a humectant.

10. The personal care composition of claim 1, wherein a weight ratio of the bis-abolol and ginger extract to the surfactant derived from olive oil is from about 0.01 to 1 to about 1 to 0.01.

11. The personal care composition of claim 1, wherein the carrier further comprises from about 4% to about 30% of a lathering surfactant by weight of the composition.

12. A method of reducing skin irritation comprising:
   a. applying a personal care composition to a portion of skin to form a treated surface, said personal care composition comprising a multi-active system for down regulating cytokines, said multi active system comprising:
      i. bis-abolol and ginger extract, and
      ii. a surfactant derived from a predominantly unsaturated triglyceride comprising sodium polyethylene glycol 7 olive oil carboxylate.

13. The method of claim 12, further comprising a step of at least partially removing hair from said at least a portion of the treated surface.

14. The method of claim 12, further comprising a step of at least partially removing hair from a portion of skin, prior to the step of applying said personal care composition to said portion of skin.

* * * * *